(12) United States Patent
Lunn et al.

(10) Patent No.: US 10,582,922 B2
(45) Date of Patent: Mar. 10, 2020

(54) KNOTLESS SUTURE ANCHOR WITH BREAKAWAY TIP

(71) Applicant: Smith & Nephew, Inc., Memphis, TN (US)

(72) Inventors: Richard M. Lunn, Memphis, TN (US); Timothy Young, Memphis, TN (US); Matthew Edwin Koski, Memphis, TN (US); Jon-Paul Rogers, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 307 days.

(21) Appl. No.: 15/739,412

(22) PCT Filed: Jun. 29, 2016

(86) PCT No.: PCT/US2016/040088
§ 371 (c)(1),
(2) Date: Dec. 22, 2017

(87) PCT Pub. No.: WO2017/011185
PCT Pub. Date: Jan. 19, 2017

(65) Prior Publication Data
US 2018/0185019 A1    Jul. 5, 2018

Related U.S. Application Data

(60) Provisional application No. 62/191,803, filed on Jul. 13, 2015.

(51) Int. Cl.
*A61B 17/04* (2006.01)
*A61B 90/00* (2016.01)

(52) U.S. Cl.
CPC .... *A61B 17/0401* (2013.01); *A61B 2017/044* (2013.01); *A61B 2017/0409* (2013.01);
(Continued)

(58) Field of Classification Search
CPC ............ A61B 17/0401; A61B 17/7216; A61B 17/7266; A61F 2/0811; A61F 2/0805;
(Continued)

(56) References Cited

U.S. PATENT DOCUMENTS

| | | | |
|---|---|---|---|
| 2013/0131723 A1* | 5/2013 | Snell | A61B 17/0401 606/232 |
| 2014/0277129 A1* | 9/2014 | Arai | A61B 17/0401 606/232 |

OTHER PUBLICATIONS

European Application No. 16736734.1-1121 Examination Report dated Dec. 20, 2018.

* cited by examiner

*Primary Examiner* — Anh T Dang
(74) *Attorney, Agent, or Firm* — Burns & Levinson LLP; Joseph M. Maraia (57) ABSTRACT

A one-piece knotless suture anchor with a breakaway distal tip is disclosed. The suture anchor includes a thin section connecting a distal anchor portion and proximal anchor portion. The thin section has a cutaway geometry allowing it to break in a repeatable manner. Force from a driver breaks the thin section connecting the distal and proximal anchor portions. The proximal anchor portion slides distally over the elongated member (either distal or proximal to the distal eyelet) and a repair suture is pinched between the distal and proximal anchor portions, or in between the bone tunnel walls and outer diameter of the sleeve, thereby fixing the repair suture in place without tying an arthroscopic knot.

28 Claims, 12 Drawing Sheets

(52) U.S. Cl.
CPC ............... *A61B 2017/0412* (2013.01); *A61B 2017/0414* (2013.01); *A61B 2017/0441* (2013.01); *A61B 2017/0445* (2013.01); *A61B 2017/0453* (2013.01); *A61B 2017/0454* (2013.01); *A61B 2090/037* (2016.02)

(58) Field of Classification Search
CPC ...... A61F 2002/0852; A61F 2002/0817; A61F 2002/0876; A61F 2017/044; A61F 2017/0409; A61F 2017/0412; A61F 2017/0411; A61F 2250/0007
See application file for complete search history.

KNOTLESS SUTURE ANCHOR WITH BREAKAWAY TIP

CROSS-REFERENCE TO RELATED APPLICATIONS

This application is the U.S. national phase entry under 35 U.S.C. § 371 of International Application No. PCT/US2016/040088, filed Jun. 29, 2016, entitled KNOTLESS SUTURE ANCHOR WITH BREAKAWAY TIP, which in turn claims priority to and benefit of U.S. Provisional Application No. 62/191,803, filed Jul. 13, 2015, the contents of which are incorporated herein by reference in their entirety for all purposes.

FIELD

The present disclosure relates to knotless suture anchors for use in arthroscopic surgery and, more particularly, to a knotless suture anchor with a breakaway tip.

BACKGROUND

Arthroscopic surgeries (such as instability, rotator cuff, Achilles tendon, gluteus medius/maximus, and hamstring repairs) require torn soft tissue to be re-attached in an anatomically correct position. Suture anchors are typically the primary source of fixation for soft tissue repairs. Suture anchors can be knotless or tied suture devices.

Problems can arise in tied suture anchors which require the surgeon to be able to tie arthroscopic knots. These knots can be difficult and time-consuming to the arthroscopic surgery. Post-operative trauma can also be caused by prominent knot stacks. Therefore, knotless suture anchors are used by surgeons who do not wish to tie arthroscopic knots. Knotless anchors allow the surgeon to place the suture anchor, adjust the repair suture to their desired tension, and then fix the repair suture in place so it is unable to slide through the suture anchor. This fixing of the repair suture is done through a secondary procedural step where the anchor compresses the suture so it is no longer able to slide though the anchor.

One example of such a knotless suture anchor known in the art includes a cannulated plug or screw pre-loaded onto a driver that includes an eyelet at its distal end. A suture attached to soft tissue or graft is passed through the eyelet. The driver and the eyelet are then inserted into a pilot hole in a bone with the plug or screw remaining just outside the hole. The screw or plug is then fully advanced into the pilot hole by tapping or twisting the interference screw or plug until the cannulated plug or screw securely engages and locks in the eyelet implant so that the cannulated plug or screw with the engaged eyelet implant is engaged with the bone. When the cannulated plug or screw is fully deployed, the suture is locked. However, the disadvantages of current suture anchors are that they require two separate components for the eyelet and cannulated plug or screw which increase assembly complexity during manufacturing. Also, the surface of the eyelet is generally smooth and does not itself provide any engagement with the bone tunnel.

SUMMARY

Described herein is a one-piece knotless anchor with a breakaway distal tip. The anchor includes a thin section connecting a distal anchor portion and proximal anchor portion. The thin section has a cutaway geometry allowing it to break in a repeatable manner. Force from a driver breaks the thin section connecting the distal and proximal anchor portions. The proximal anchor portion slides distally over the thin section and a repair suture is pinched between the distal and proximal anchor portions, thereby advantageously fixing the repair suture in place without tying an arthroscopic knot. Alternatively, the suture may be pinched in between the advanced proximal portion of the anchor and inner walls of the bone tunnel.

Examples of the suture anchor include a suture anchor having a sleeve with a plurality of threads, which may be helical, along a longitudinal axis, an elongate member extending from a distal end of the sleeve, along the longitudinal axis, the elongate member being coupled to the sleeve by a break-away coupling, and a tip extending from a distal end of the elongate member, the tip being rigidly coupled to the elongate member. The sleeve, the elongate member, and the tip are rotationally coupled when the break-away coupling is intact and the sleeve is rotationally decoupled from the elongate member and tip when the break-away coupling is broken. The sleeve also has a first lumen, while the elongate member has a second lumen, the first and second lumens being co-axial with one another. The inner diameter of the first lumen of the sleeve is greater than the outer diameter of the elongate member so that when the break-away coupling is broken, the sleeve is adapted to slide over the outer surface of the elongate member between a first position, where the distal end of the sleeve is positioned proximal to the eyelet, and a second position, where the distal end of the sleeve is positioned distal to the eyelet.

Further examples of the suture anchor include a suture anchor having an eyelet extending through one of the elongate member and the tip. A suture extends through the eyelet, with the suture being interposed between the outer diameter of the elongate member and the inner diameter of the sleeve when the sleeve is in the second position. Alternatively, the suture may be interposed between the proximal portion of the anchor sleeve and inner walls of the bone tunnel with the anchor in the second position. The plurality of threads of the sleeve are spaced apart by first openings in communication with the first lumen. The elongate member also has a plurality of second openings in communication with the second lumen, so that the first and second openings are dimensioned to align when the sleeve is in the second position. This plurality of openings may align, advantageously permitting an open architecture anchor and thus promoting bony in-growth through the fenestrations and into the body of the anchor. The break-away coupling consists of a region of reduced cross-sectional area between the proximal end of the elongate member and the distal end of the sleeve or a plurality of ligaments spaced apart by cut-out regions extending transverse to the longitudinal axis through the elongate member, the ligaments connecting the proximal end of the elongate member to the distal end of the sleeve. Alternatively, the plurality of ligaments may be at an angle to the longitudinal axis. The break-away coupling is adapted to separate the elongate member from the sleeve upon application of an axial force and/or torque greater than a selected level at the break-away coupling.

Examples of the suture anchor assembly include an anchor as described above, together with an anchor driver having an elongate body and a driver tip positioned at a distal end of the driver body. The driver tip includes a first portion dimensioned for receipt within the first lumen of the anchor and a second portion, distal to the first portion, dimensioned for receipt within the second lumen of the anchor. The first portion of the driver tip and the inner walls of the first lumen are adapted to mate such the first portion of the driver tip is capable of transmitting a n axial and/or rotational force to the sleeve. The second portion of the driver tip is dimensioned to contact the proximal end of the tip such that the second portion of the driver tip is capable of transmitting an axial and or rotational force to the anchor tip. The second portion of the driver tip and the inner walls of the second lumen are adapted to mate such the second portion of the driver tip is capable of transmitting a rotational force to the elongate member.

Examples of the method of anchoring a suture include the steps of creating a bone tunnel with other ancillary devices, passing suture through the desired tissue repair site, providing a suture anchor as described above, inserting a suture within the eyelet of the suture anchor, inserting the anchor into the bone tunnel, breaking the break-away coupling and distally advancing the sleeve over the outer surface of the elongate member to a position where the distal end of the sleeve is distal to the eyelet, with the suture interposed between the outer diameter of the elongate member and the inner diameter of the sleeve in the second position of the sleeve, or the suture interposed between the outer diameter of the sleeve and inner diameter of the bone tunnel wall. The tip and elongate member are axially and rotationally decoupled from the sleeve when the break-away coupling is broken. Distally advancing the sleeve includes rotationally advancing the threads through the bone hole surrounding the suture anchor while retaining the anchor tip and elongate member in place. Breaking the break-away coupling includes applying at least one of an axial force and/or torque greater than a selected level, to the first portion of the sleeve, while rigidly fixing the anchor tip. Distally advancing the sleeve further includes moving the sleeve into the second position. Optionally, a portion of the first and second openings which may or may not be present in the suture anchor are longitudinally aligned. Advantageously, the first portion of the driver tip and the second portion of the driver tip can rotate/translate independently of each other in order to transmit the necessary forces and reaction forces on the anchor body in order to break the anchor in a consistent manner.

The foregoing and other objects, features and advantages will be apparent from the following more particular description of the embodiments,

BRIEF DESCRIPTION OF THE DRAWINGS

FIGS. 2-3B are illustrations of an alternate examples of the suture anchor;

FIGS. 4A-5B are illustrations of the break-away coupling of the suture anchor;

FIGS. 8A-9F are illustrations of an alternate examples of the suture anchor and driver.

DETAILED DESCRIPTION

In the description that follows, like components have been given the same reference numerals, regardless of whether they are shown in different examples. To illustrate an example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

The terms "comprise," "include," and/or plural forms of each are open ended and include the listed parts and can include additional parts that are not listed. "And/or" is open ended and includes one or more of the listed parts and combinations of the listed parts.

Figure 1A:
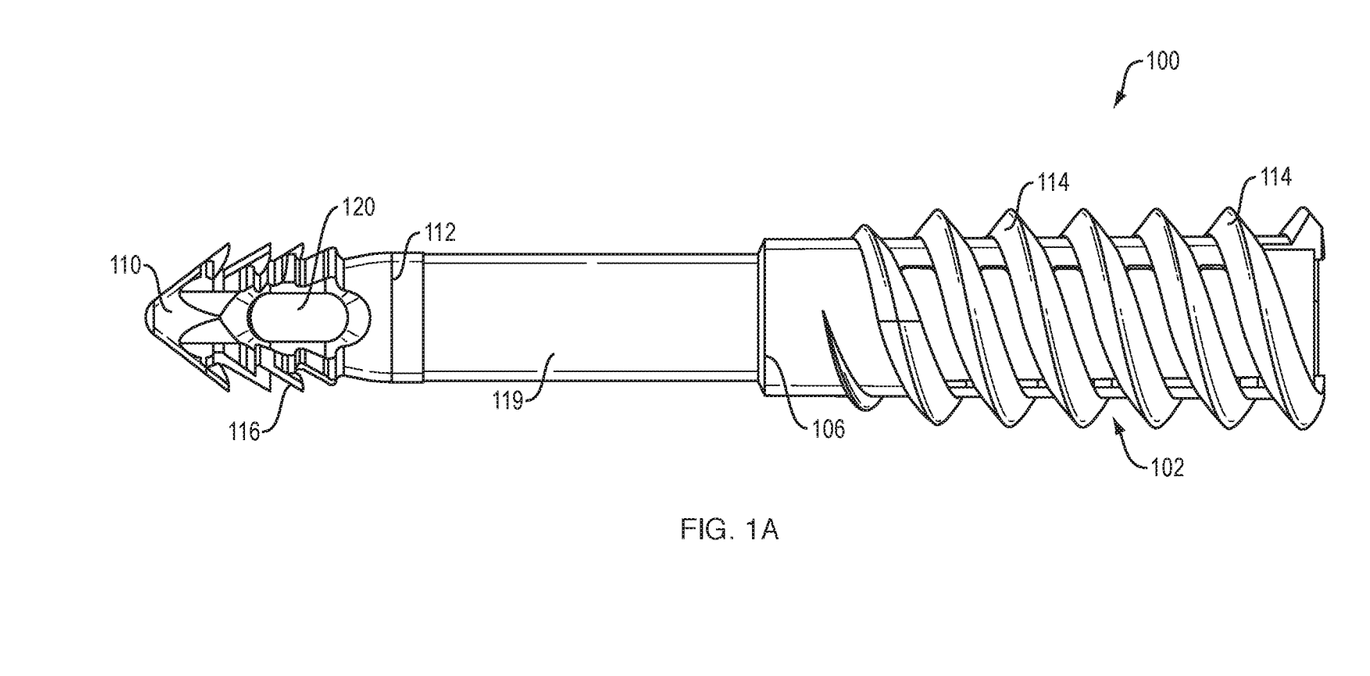
FIG. 1A is an illustration of a suture anchor of the present disclosure.

Referring now to FIG. 1A, and example of the suture anchor 100 of this disclosure includes a sleeve 102 having threads 114, and an elongate member 119 extending distally from sleeve 102. The threads 114 are shown as helical but may be any other geometry that can generate fixation within a bone tunnel (e.g. stacks of barbs). The anchor 100 may be a screw-in or pound-in design. The elongate member 119 is coupled to the sleeve 102 by a break-away coupling 106, as further described below. A tip 110 is rigidly coupled to the elongate member 119 at the opposite end from the break-away coupling 106. The tip 110 has a distal, barbed portion 116 and a proximal, non-barbed portion 112. Transverse eyelet 120 is shown as located in the barbed portion 116 for passing sutures therethrough, although the eyelet 120 may also be located in the non-barbed portion 112. The sleeve 102, the elongate member 119, and the tip 110 are rotationally coupled when the break-away coupling 106 is intact, while the sleeve 102 is rotationally decoupled from the elongate member 119 and the tip 110 when the break-away coupling 106 is broken. Also contemplated by this disclosure are examples of the tip 110 being fixed or rotatable, or capable or being screwed into a bone hole via threads, barbs or other suitable means. Alternatively or additionally, the proximal end of the sleeve 102 could rotate during the insertion process while breaking the break-away coupling 106 and then screwing the sleeve 102 into the bone hole.

Figure 1B:
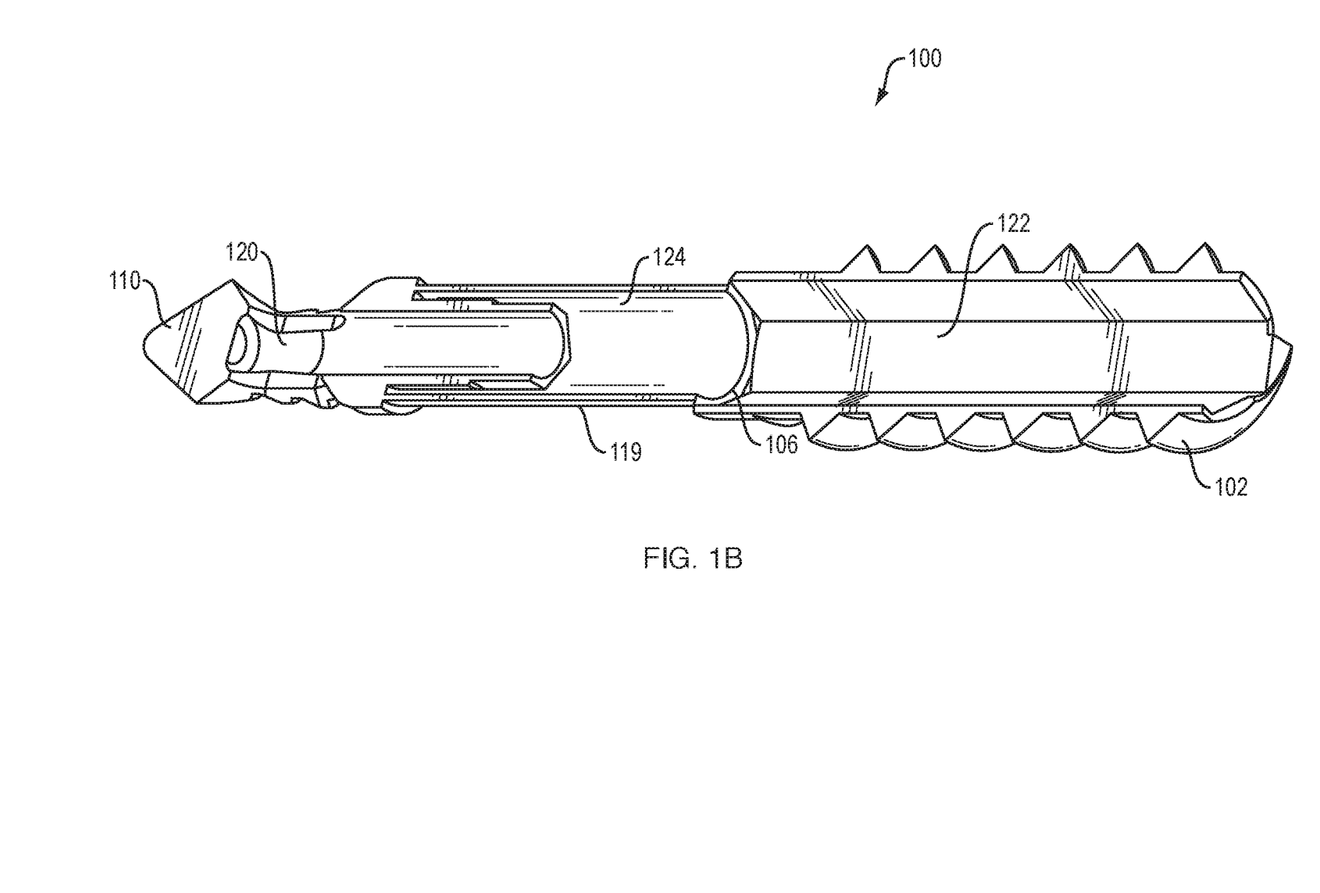
FIG. 1B is a sectional view of the suture anchor of FIG. 1A.
Figure 1C:
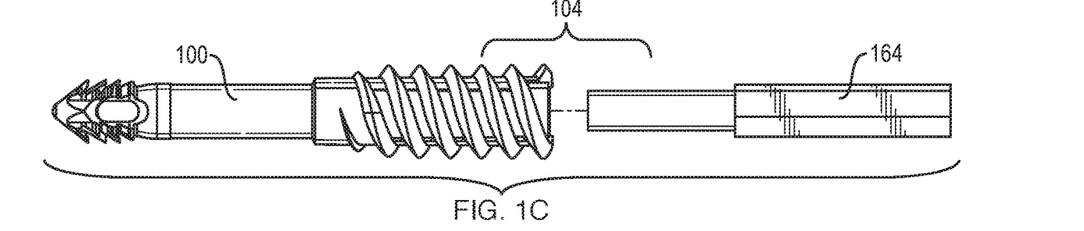
FIGS. 1C-H are additional views of the suture anchor of FIG. 1A together with a driver.
Figure 1D:
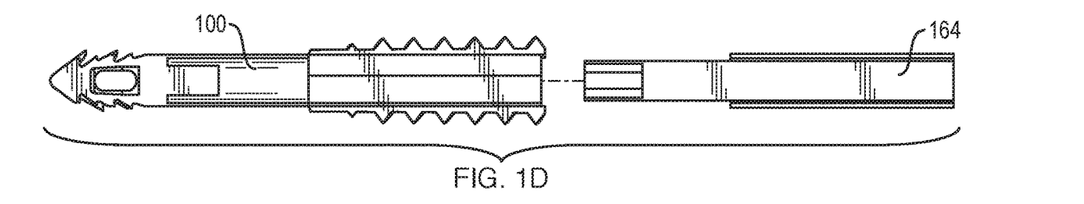
Figure 1E:
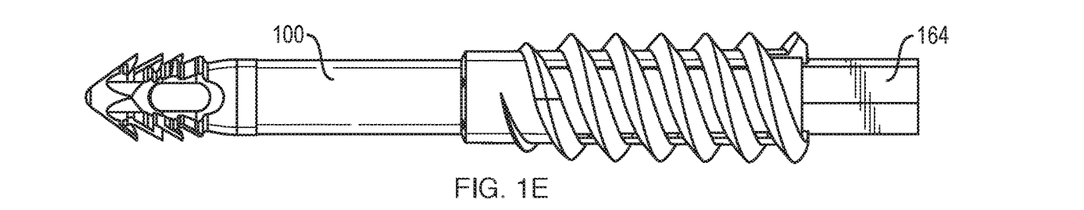
Figure 1F:
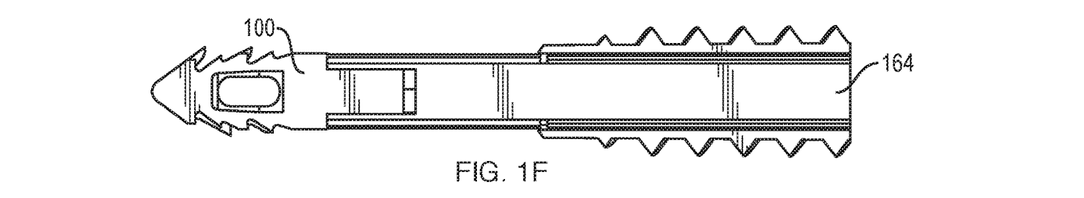
Figure 1G:
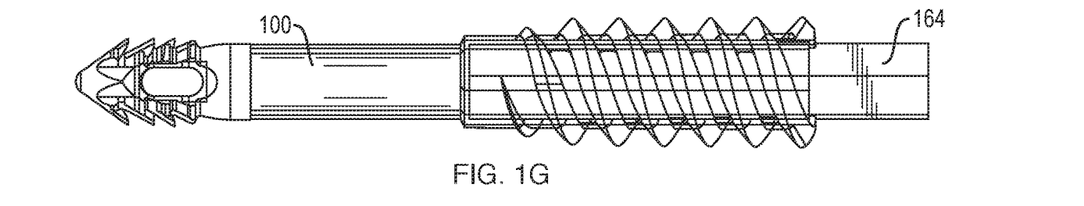

FIG. 1B shows a cut-away view of the sleeve 102, the elongate member 119 and the tip 110 of the embodiment of FIG. 1a. The sleeve 102 includes a first lumen 122 and the elongate member 119 includes a second lumen 124. The first and second lumens 122, 124 are co-axial with one another. The inner diameter of the first lumen 122 is greater than the outer diameter of the elongate member 119. Therefore, when the break-away coupling 106 is broken, the sleeve 102 is capable of sliding over the outer surface of the elongate member 119 between a first position, where the distal end of the sleeve 102 is positioned proximal to the eyelet 120, and a second position, where the distal end of the sleeve 102 is positioned distal to the eyelet 120. Alternatively, the sleeve 102 may be slid over the elongate member 119 to an alternative location between the first and second position, where the distal end of the sleeve 102 is positioned proximal to a distal terminus of the eyelet 120, as long as the proximal end of the sleeve 122 is set below the surface of the bone tunnel. In this case, the suture may be interposed between the outer diameter of the sleeve 102 and the inner walls of the bone tunnel.

Figure 1H:
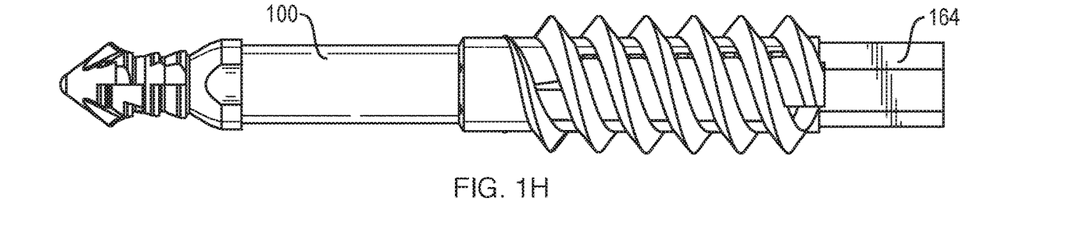

FIGS. 1C-H show additional views of the suture anchor 100 with an anchor driver 164, together forming an anchor/driver system 104. The views shown are an exploded view (FIG. 1C), a cross-section of the exploded view (FIG. 1D), an assembled view (FIG. 1E), a cross-section of the assembled view (FIG. 1F), an assembled view with the suture anchor 100 shown as transparent (FIG. 1G) and the suture anchor 100 of FIG. 1A rotated 90 degrees (FIG. 1H). Examples of the anchor driver 164 will be described in more detail below.

Figure 2:
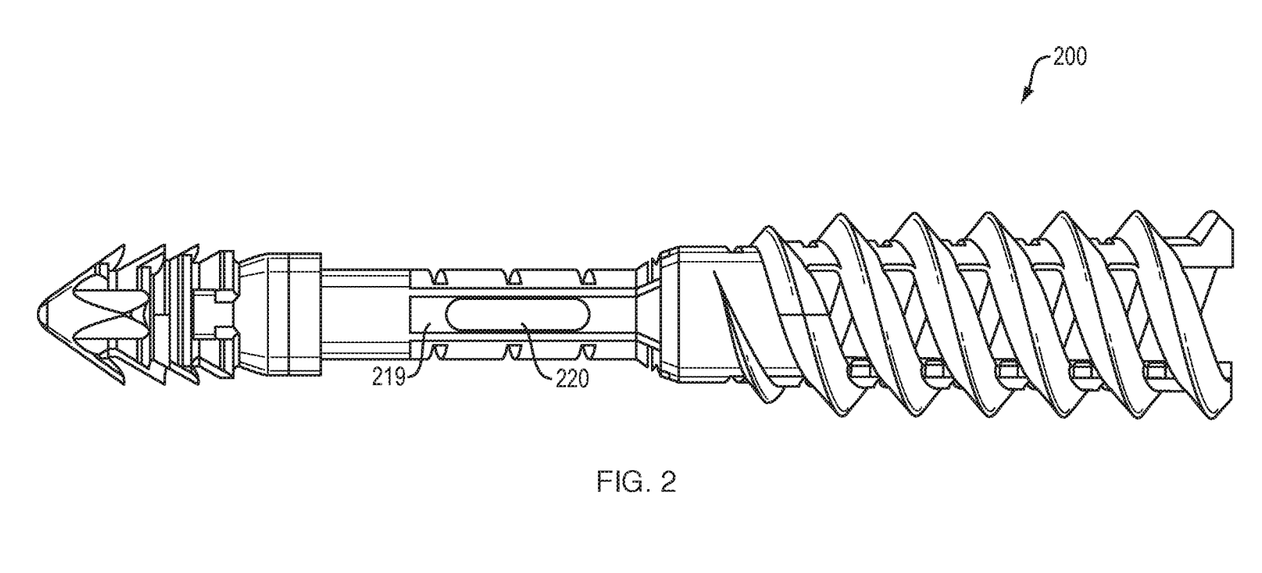
Figure 3A:
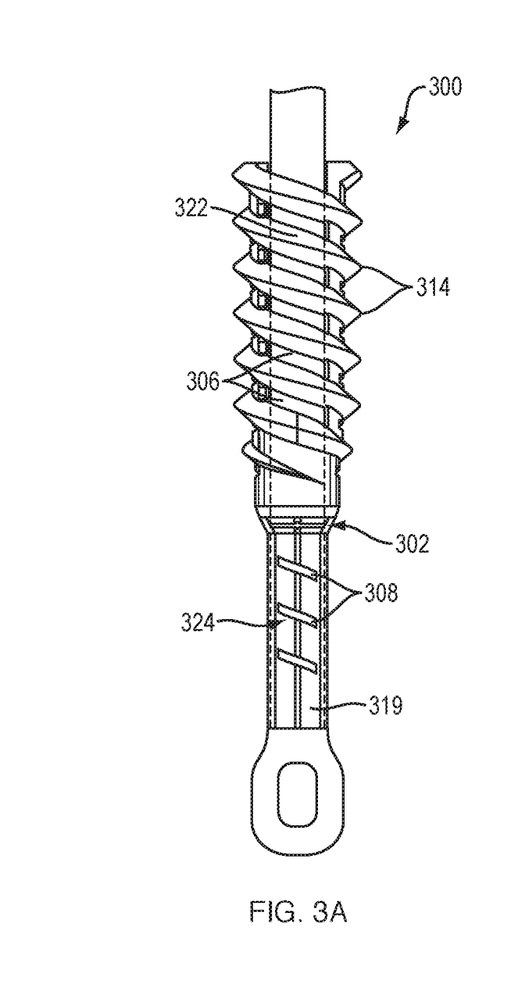
Figure 3B:
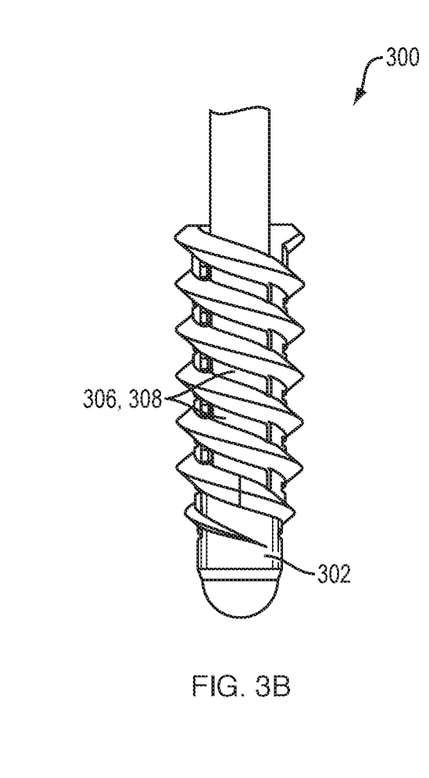

FIGS. 2-3B illustrate further examples of the suture anchor 200 and 300. In FIG. 2, the transverse eyelet 220 is shown as located in the elongate member 219. In FIG. 3a the plurality of threads 314 of the sleeve 302 are spaced apart by first openings 306 in communication with the first lumen 322. The elongate member 319 further has a plurality of second openings 308 in communication with the second lumen 324. As shown in FIG. 3B, when the sleeve 302 is moved into in the second position, the first and second openings 306, 308 are dimensioned to align. Advantageously, the openings 306, 308 provide a space for bony ingrowth into the suture anchor 300, which improves fixation strength of the suture anchor 300 and promotes better healing.

Figure 4A:
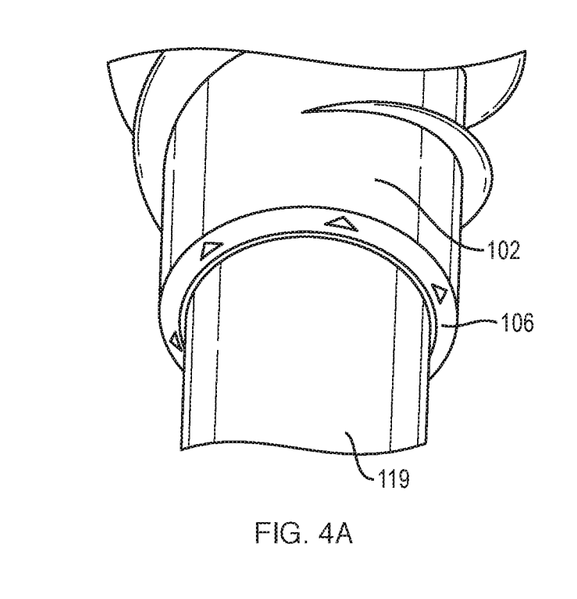
Figure 4B:
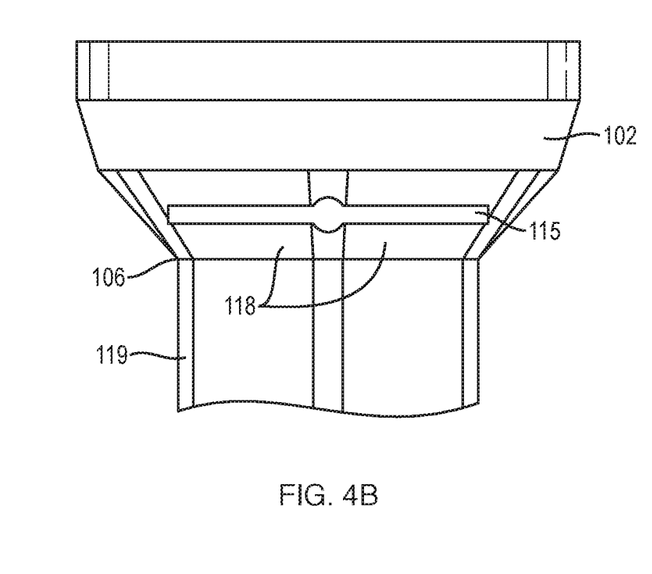
Figure 5A:
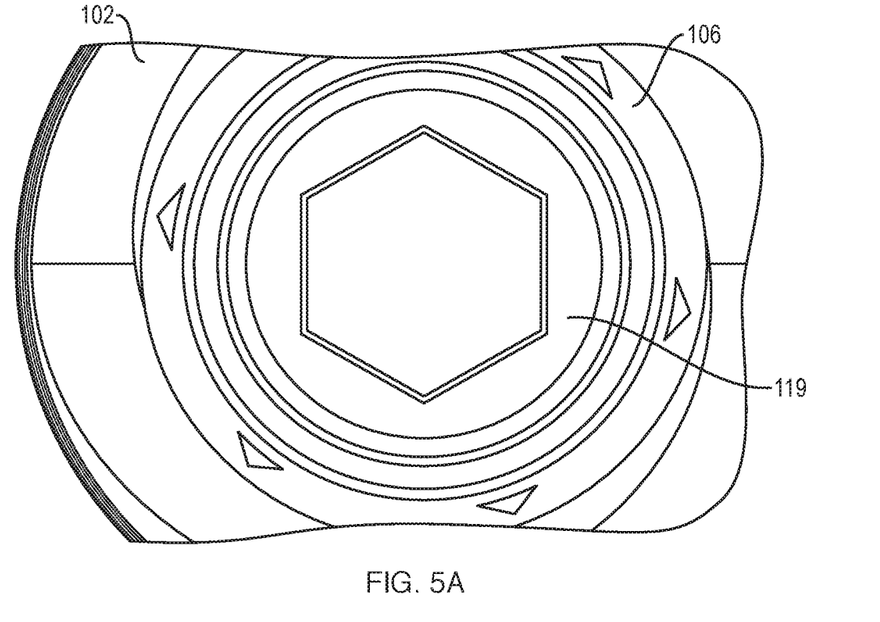
Figure 5B:
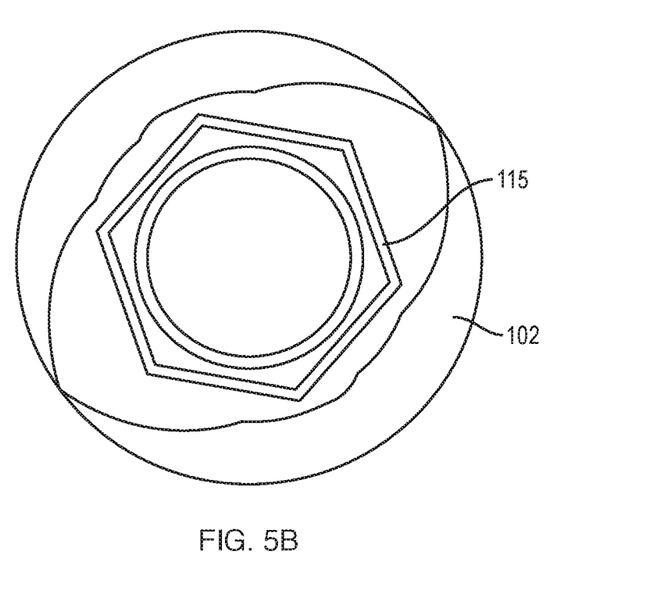

Turning now to FIG. 4A, a detailed illustration of the break-away coupling 106 of the suture anchor 100 is shown. The break-away coupling 106 includes a reduced cross-sectional area between the proximal end of the elongate member 119 and the distal end of the sleeve 102. The break-away coupling 106 is adapted to separate the elongate member 119 from the sleeve 102 upon application of enough axial force and/or torque to break the break-away coupling 106. In an alternative example shown in FIG. 4B, the break-away coupling 106 has a plurality of ligaments 118 spaced apart by cut-out regions 115 extending transverse to the longitudinal axis through the elongate member 119, the ligaments connecting the proximal end of the elongate member 119 to the distal end of the sleeve 102. Alternatively, the cut out regions 115 may also be placed at an angle to a transverse longitudinal axis of the elongated member 119. FIGS. 5A and 5B illustrate section views of the break-away coupling 106. That is, FIG. 5A shows a section view of the break-away coupling 106 of FIG. 4A, and FIG. 5B shows a section view of the break-away coupling 106 of FIG. 4B.

Figure 6A:
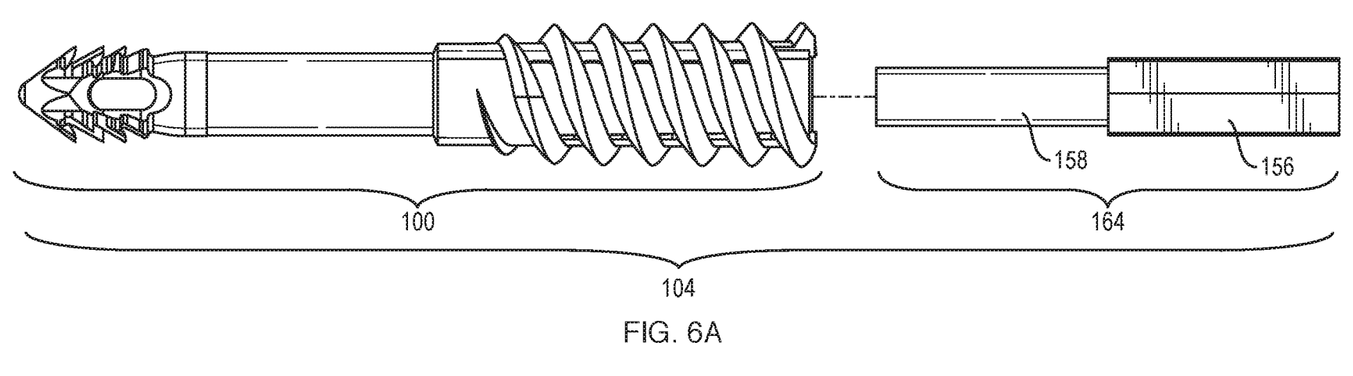
FIGS. 6A-6B are further views of the suture anchor assembly of FIGS. 1C-H.
Figure 6B:
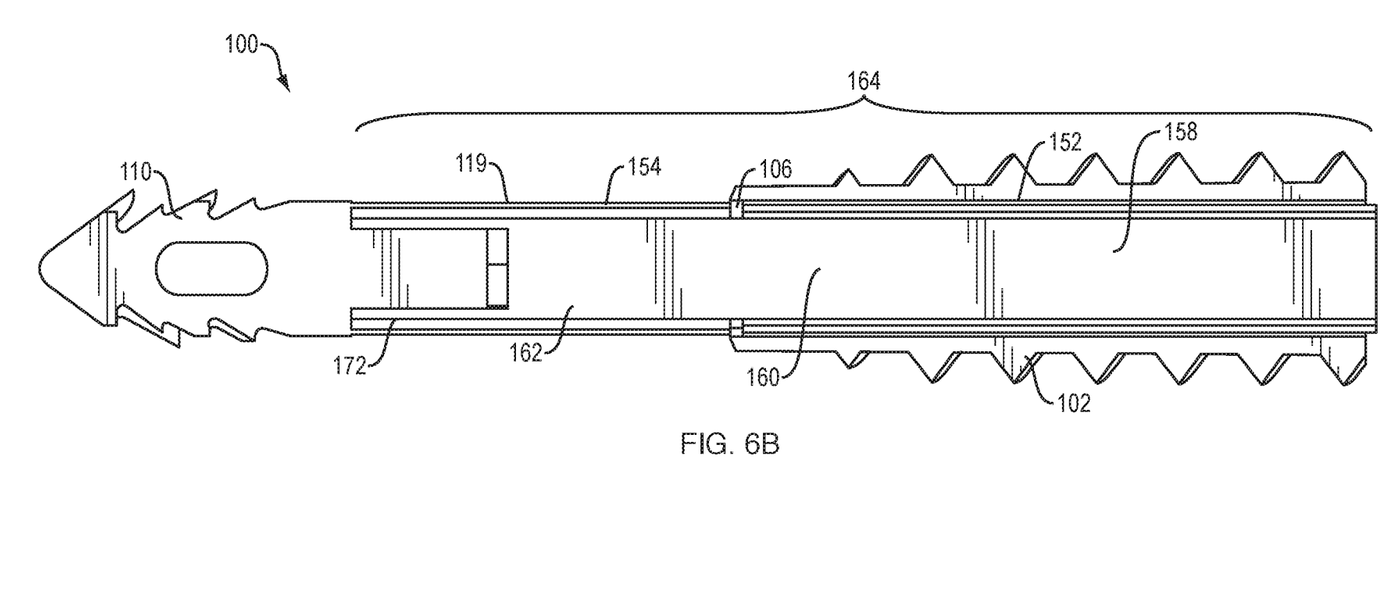

FIGS. 6A and 6B show an example of the suture anchor 100 as described in FIGS. 1A-H, and an anchor driver 164, together forming the anchor/driver system 104. As shown in FIG. 6A, the anchor driver 164 includes a driver body 156 and a driver tip 158 positioned at a distal end of the driver body 156. As shown in FIG. 6B, the driver tip 158 includes a first portion 160 dimensioned for receipt within the first lumen 152 of the sleeve 102, and a second portion 162 extending distally from the first portion 160, dimensioned for receipt within the second lumen 154 of the elongated member 119. The first portion 160 of the driver tip 158 and the inner walls of the first lumen 152 are adapted to mate such that the first portion 160 of the driver tip 158 is capable of transmitting a rotational force to the sleeve 102 when the driver 164 is turned. The second portion 162 of the driver tip 158 is dimensioned to contact the proximal end of the anchor tip 110 such that the second portion 162 of the driver tip 158 is capable of transmitting an axial force to the anchor tip 110 when the driver 164 is turned. The second portion 162 of the driver tip 158 and the inner walls of the second lumen 154 are also adapted to mate such the second portion 162 of the driver tip 158 is capable of transmitting a rotational force to the elongate member 119 when the driver 164 is turned. The first portion 160 of the driver 158 and the second portion 162 of the driver tip 158 are able to rotate and/or translate independently of each other in order to apply the necessary reaction forces on the suture anchor 100 to break the break-away coupling 106. The second portion 162 may also have a third portion 172 comprising, for example, prongs dimensioned for receipt within mating slots of the distal tip area of the suture anchor 100. This configuration advantageously may provide further stability to the tip 110 during insertion into bone or during decoupling of the break-away coupling 106.

Figures 7A, 7B:
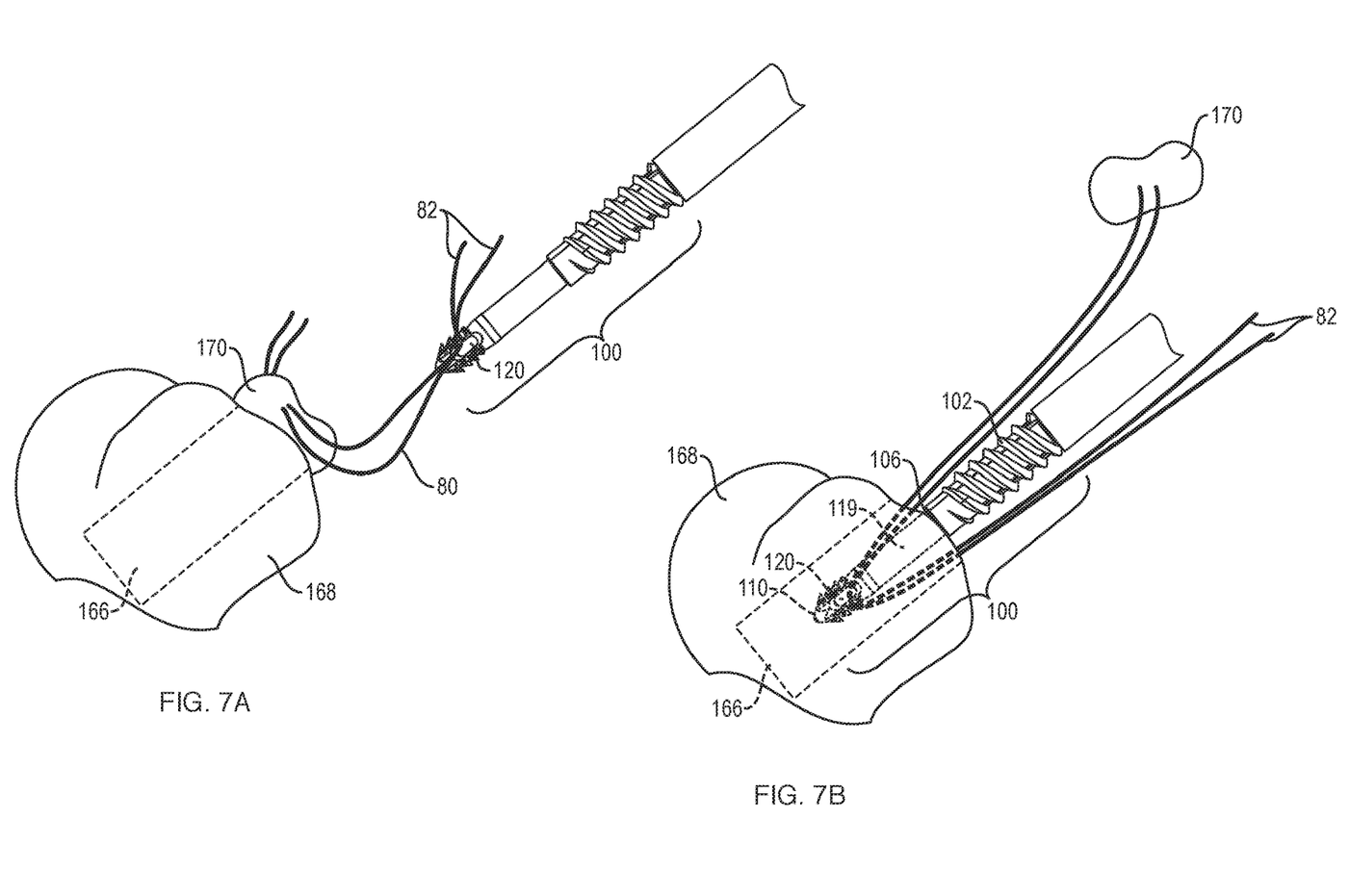
FIGS. 7A-C are illustrations of an example of the method of the present disclosure.
Figure 7C:
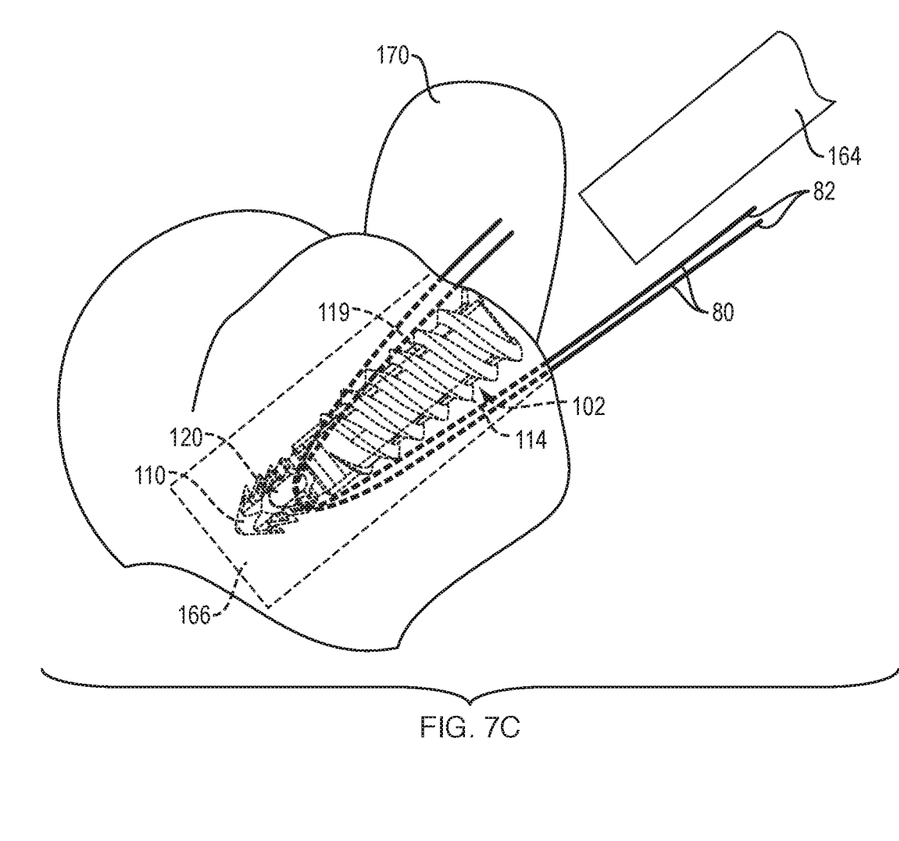
Figure 8A:
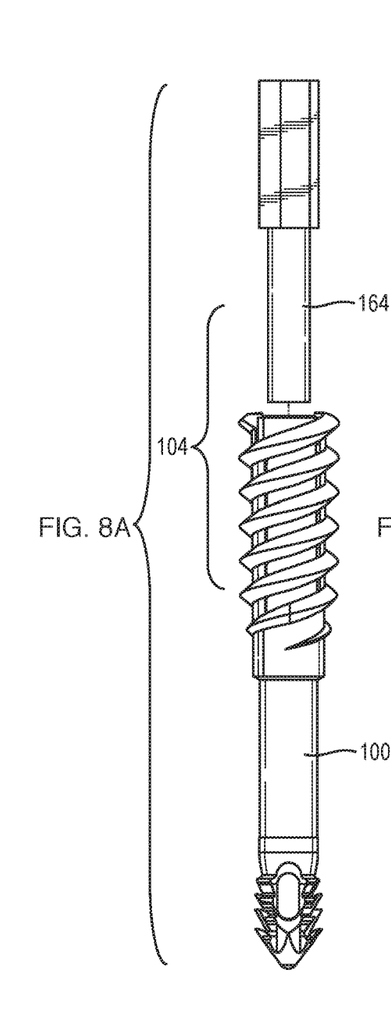
Figure 8B:
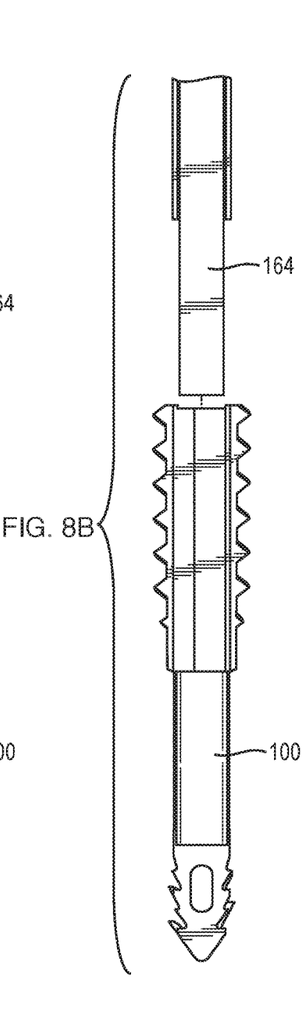
Figure 8C:
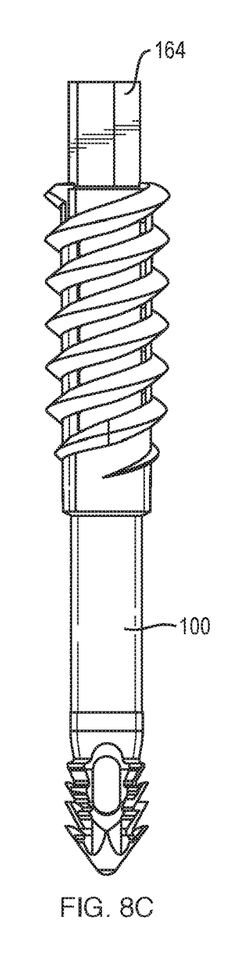
Figure 8D:
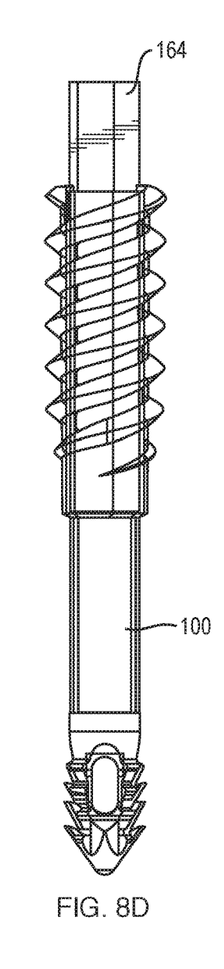
Figure 8E:
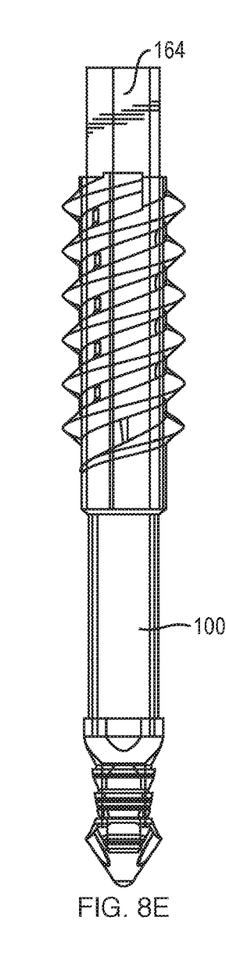

Described herein is also a method for securing soft tissue to bone, which is illustrated in FIGS. 7A-C. As shown in FIG. 7A, a bone hole or socket 166 is created in a bone 168 at the location that a graft or tissue 170 is to be secured. Free ends 82 of a suture 80 are passed through the tissue or graft 170 at the desired points. The free ends 82 of the suture 80 are then passed through the eyelet 120 of the suture anchor 100. As shown in FIG. 7B, the suture anchor 100 including the eyelet 120 is inserted into the bone hole 166 to the desired depth, with the sleeve 102 disposed just outside the bone hole 166. Tension is applied to the suture 80 to position the tissue 170 at the desired location relative to the bone hole 166. Once an adequate level of tension is achieved, the break-away coupling 106 is broken by applying a sufficient axial force and/or torque at the break-away coupling 106 so that and the tip 110 and elongate member 119 are axially and rotationally decoupled from the sleeve 102. As shown in FIG. 7C, the sleeve 102 is then advanced distally over the outer surface of the elongate member 119 by advancing the threads 114 through the bone hole 166 surrounding the sleeve 102 while retaining the anchor tip 110 and elongate member 119 in place. The sleeve 102 is advanced in this manner to a position where the distal end of the sleeve 102 is distal to the eyelet 120 and wherein the suture 80 is interposed between the outer diameter of the elongate member 119 and the inner diameter of the sleeve 102. Alternatively, the sleeve 102 may be advanced so that the distal end of the sleeve 102 is proximal to the eyelet 120 and the suture 80 may instead be impinged between the threads 114 of the sleeve 102 and the bone hole 166. Once the sleeve 102 is fully inserted and the suture 80 is rigidly secured within the bone hole 166, the driver 164 is removed and the free ends 82 ends of the sutures 80 protruding from the bone hole 166 are clipped short as close to the anchor 100 as possible.

Figure 9A:
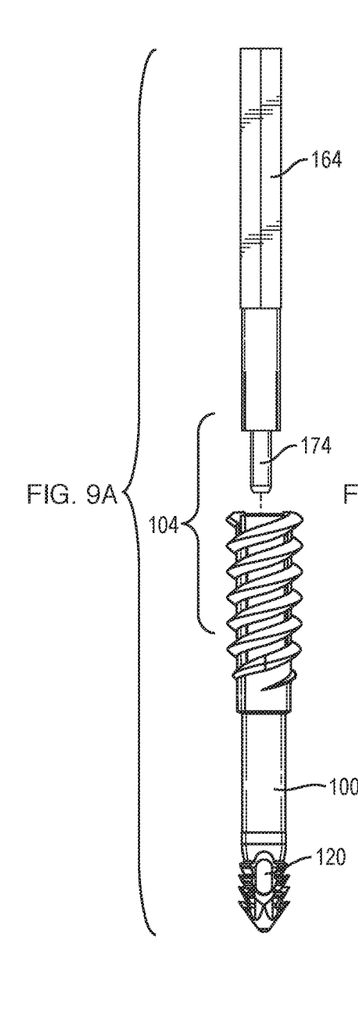
Figure 9B:
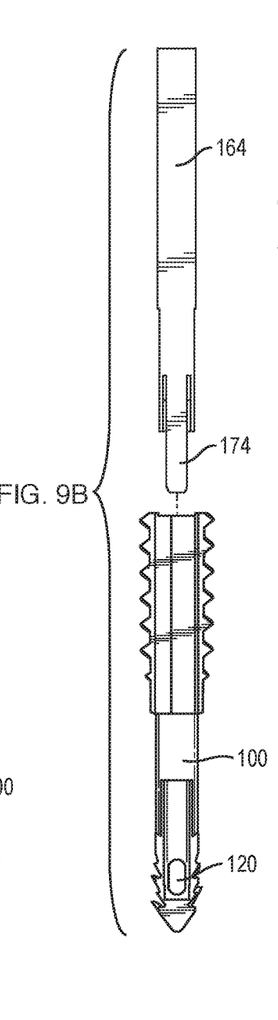
Figure 9C:
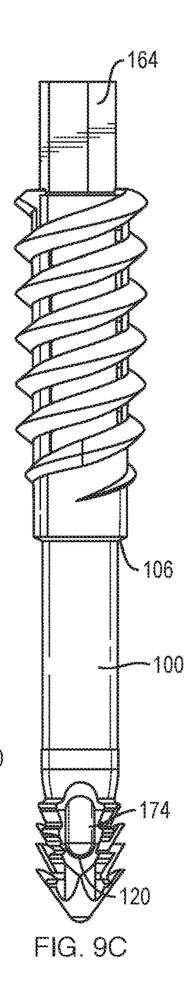
Figure 9D:
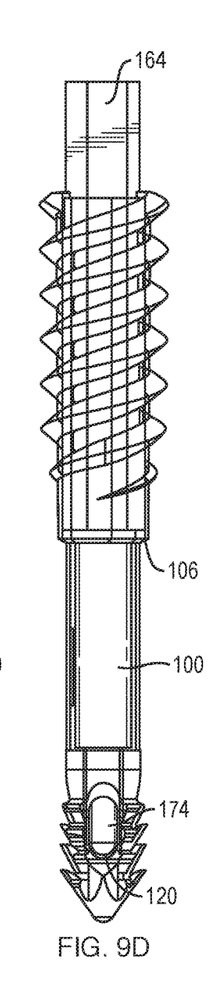
Figure 9E:
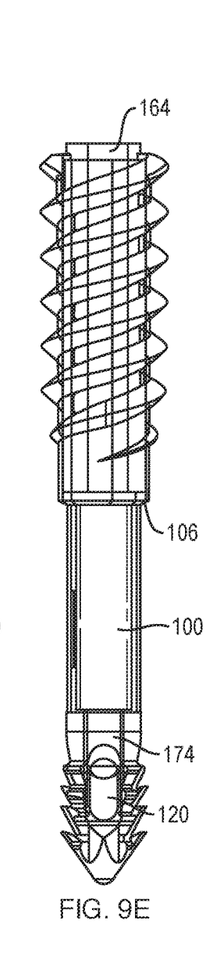
Figure 9F:
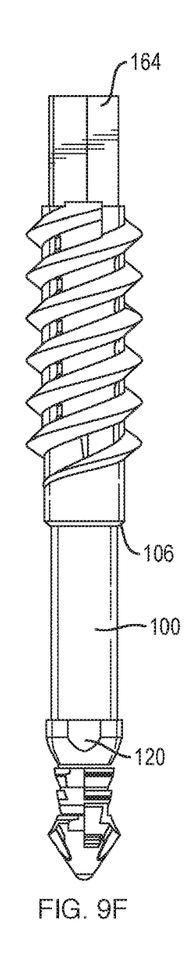

FIGS. 8A-E and 9A-F show alternative examples of the anchor/driver system 104. In FIGS. 8A-E, the driver 164 is shown without the third pronged portion 172 (FIG. 6B). The views shown are an exploded view (FIG. 8A), a cross-section of the exploded view (FIG. 8B), an assembled view (FIG. 8C), an assembled view with the suture anchor 100 shown as transparent (FIG. 8D) and the suture anchor 100 of FIG. 1A rotated 90 degrees (FIG. 1H). In FIGS. 9A-F, the driver 164 includes an additional inner plug 174. The views shown are an exploded view (FIG. 9A), a cross-section of the exploded view (FIG. 9B), an assembled view (FIG. 9C), an assembled view with the suture anchor 100 shown as transparent with the inner plug 174 extended (FIG. 9D), an assembled view with the suture anchor 100 shown as transparent with the inner plug 174 slightly retracted (FIG. 9E), and the suture anchor 100 of FIG. 9A rotated 90 degrees (FIG. 9F). As particularly shown in FIG. 9E, the inner plug 174 can be variably retracted to allow for space in the eyelet 120 for suture placement or adjustment when loading sutures, or while tensioning sutures before decoupling the break-away coupling 106.

One skilled in the art will realize that embodiments of the disclosure may be embodied in alternative forms without departing from the spirit or essential characteristics thereof. The foregoing embodiments are therefore to be considered in all respects illustrative rather than limiting of the invention described herein. Scope of the disclosed embodiments is thus indicated by the appended claims, rather than by the foregoing description, and all changes that come within the meaning and range of equivalency of the claims are therefore intended to be embraced therein.

The invention claimed is:

1. A suture anchor comprising:
   a sleeve having a plurality of threads and defining a longitudinal axis;
   an elongate member extending from a distal end of the sleeve, along the longitudinal axis, the elongate member being coupled to the sleeve by a break-away coupling; and
   a tip extending from a distal end of the elongate member, the tip being rigidly coupled to the elongate member;
   wherein the sleeve, the elongate member, and the tip are rotationally coupled when the break-away coupling is intact; and
   wherein the sleeve is rotationally decoupled from the elongate member and tip when the break-away coupling is broken.

2. The suture anchor of claim 1, wherein the sleeve comprises a first lumen and the elongate member comprises a second lumen co-axial with the first lumen.

3. The suture anchor of claim 2, wherein an inner diameter of the first lumen of the sleeve is greater than an outer diameter of the elongate member.

4. The suture anchor of claim 3, further comprising:
   an anchor driver comprising an elongate body and a driver tip positioned at a distal end of the driver body, the driver tip further including:
   a first portion dimensioned for receipt within the first lumen of the sleeve; and
   a second portion, distal to the first portion, dimensioned for receipt within the second lumen of the elongate member.

5. The system of claim 4, wherein the first portion of the driver tip and inner walls of the first lumen are adapted to mate such the first portion of the driver tip is capable of transmitting a rotational and/or axial force to the sleeve.

6. The system of claim 5, wherein the second portion of the driver tip and inner walls of the second lumen are adapted to mate such the second portion of the driver tip is capable of transmitting a rotational force to the elongate member.

7. The system of claim 4, wherein the second portion of the driver tip is dimensioned to contact a proximal end of the anchor tip such that the second portion of the driver tip is capable of transmitting an axial and/or rotational force to the anchor tip.

8. The suture anchor of claim 2, wherein the plurality of threads of the sleeve are spaced apart by first openings in communication with the first lumen and wherein the elongate member further comprises a plurality of second openings in communication with the second lumen.

9. The suture anchor of claim 8, wherein the first and second openings are dimensioned to align when the sleeve is in a second position.

10. The suture anchor of claim 1, further comprising an eyelet extending through one of the elongate member and the tip.

11. The suture anchor of claim 10, wherein, when the break-away coupling is broken, the sleeve is adapted to slide over an outer surface of the elongate member between a first position, where the distal end of the sleeve is positioned proximal to the eyelet, and a second position, where the distal end of the sleeve is positioned distal to the eyelet.

12. The suture anchor of claim 10, further comprising one or more sutures extending through the eyelet, wherein the suture is interposed between an outer diameter of the elongate member and an inner diameter of the sleeve when the sleeve is in the second position.

13. The suture anchor of claim 10, wherein, when the break-away coupling is broken, the sleeve is adapted to slide over the outer surface of the elongate member between a first position, where the distal end of the sleeve is positioned proximal to the eyelet, and an alternative position, where the distal end of the sleeve is positioned proximal to a distal terminus of the eyelet.

14. The suture anchor of claim 10, further comprising one or more sutures extending through the eyelet, wherein the suture is interposed between the plurality of threads of the sleeve and surrounding bone.

15. The suture anchor of claim 1, wherein the break-away coupling comprises a region of reduced cross-sectional area between a proximal end of the elongate member and a distal end of the sleeve.

16. The suture anchor of claim 1, wherein the break-away coupling comprises a plurality of ligaments spaced apart by cut-out regions extending transverse through or at an angle to the longitudinal axis of the elongate member, the ligaments connecting a proximal end of the elongate member to a distal end of the sleeve.

17. The suture anchor of claim 1, wherein the break-away coupling is adapted to separate the elongate member from the sleeve upon application of an axial force and/or a torque greater than a selected level at the break-away coupling.

18. A method of anchoring a suture, comprising:
   providing a suture anchor comprising:
   a sleeve extending along a longitudinal axis, the sleeve having a plurality of threads and defining a first lumen;
   an elongate member extending from a distal end of the sleeve, along the longitudinal axis, the elongate member being coupled to the sleeve by a break-away coupling;
   a tip extending from a distal end of the elongate member, the tip being rigidly coupled to the elongate member; and
   an eyelet formed in one of the elongate member and the sleeve;
   inserting one or more sutures within the eyelet;
   breaking the break-away coupling; and
   distally advancing the sleeve over an outer surface of the elongate member.

19. The method of claim 18, wherein the tip and elongate member are axially and rotationally decoupled from the sleeve when the break-away coupling is broken.

20. The method of claim 19, further comprising, prior to breaking the break-away coupling, inserting the suture anchor and the one or more sutures into a bone hole.

21. The method of claim 20, wherein distally advancing the sleeve comprises rotationally advancing the threads through the bone hole surrounding the suture anchor tip and elongate member which are retained in place.

22. The method of claim 19, wherein distally advancing the sleeve over the outer surface of the elongate member comprises distally advancing the sleeve to a position where the distal end of the sleeve is distal to the eyelet, wherein the suture is interposed between the outer diameter of the elongate member and the inner diameter of the sleeve in the second position of the sleeve.

23. The method of claim 19, wherein distally advancing the sleeve over the outer surface of the elongate member comprises distally advancing the sleeve to a position where the distal end of the sleeve is proximal to a distal terminus of the eyelet, wherein the suture is interposed between the plurality of threads of the sleeve and surrounding bone in the alternative position of the sleeve.

24. The method of claim 18, wherein breaking the break-away coupling comprises applying at least one of an axial force and/or a torque greater than a selected level at the break-away coupling.

25. The method of claim 18, wherein the plurality of threads of the sleeve are spaced apart by first openings in communication with the first lumen and wherein the elongate member further comprises a plurality of second openings in communication with a second lumen formed within the elongate member.

26. The method of claim 25, wherein distally advancing the sleeve further comprises moving the sleeve into the second position such that at least a portion of the first and second openings are longitudinally aligned.

27. The method of claim 18, wherein the suture anchor further comprises a break-away coupling formed as a region of reduced cross-sectional area between a proximal end of the elongate member and a distal end of the sleeve.

28. The method of claim 18, wherein the suture anchor further comprises a break-away coupling formed as a plurality of ligaments spaced apart by cut-out regions extending transverse through or at an angle to the longitudinal axis of the elongate member, the ligaments connecting a proximal end of the elongate member a the distal end of the sleeve.

\* \* \* \* \*